US010617784B2

(12) United States Patent
Yu et al.

(10) Patent No.: US 10,617,784 B2
(45) Date of Patent: *Apr. 14, 2020

(54) ANTI-MICROBIAL ARTICLES AND METHODS OF USING SAME

(71) Applicant: 3M INNOVATIVE PROPERTIES COMPANY, St. Paul, MN (US)

(72) Inventors: Ta-Hua Yu, Woodbury, MN (US); Döne Demirgöz, St. Paul, MN (US); Junkang J. Liu, Woodbury, MN (US); Badri Veeraraghavan, Woodbury, MN (US); Narina Y. Stepanova, Inver Grove Heights, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/775,473

(22) PCT Filed: Nov. 3, 2016

(86) PCT No.: PCT/US2016/060317
§ 371 (c)(1),
(2) Date: May 11, 2018

(87) PCT Pub. No.: WO2017/083166
PCT Pub. Date: May 18, 2017

(65) Prior Publication Data
US 2018/0353638 A1 Dec. 13, 2018

Related U.S. Application Data

(60) Provisional application No. 62/254,762, filed on Nov. 13, 2015.

(51) Int. Cl.
| | | |
|---|---|---|
| A61F 13/00 | (2006.01) | |
| A61L 15/18 | (2006.01) | |
| A61L 15/46 | (2006.01) | |
| A61L 15/42 | (2006.01) | |
| A61L 15/58 | (2006.01) | |
| A61L 15/60 | (2006.01) | |

(52) U.S. Cl.
CPC ............ A61L 15/18 (2013.01); A61L 15/42 (2013.01); A61L 15/425 (2013.01); A61L 15/46 (2013.01); A61L 15/58 (2013.01); A61L 15/60 (2013.01); A61L 2300/102 (2013.01); A61L 2300/104 (2013.01); A61L 2300/404 (2013.01); A61L 2300/602 (2013.01)

(58) Field of Classification Search
None
See application file for complete search history.

(56) References Cited

U.S. PATENT DOCUMENTS

| | | | |
|---|---|---|---|
| 3,389,827 A | 1/1968 | Abere | |
| 3,415,920 A | 12/1968 | Lee | |
| 3,416,525 A | 12/1968 | Yeremain | |
| 3,645,835 A | 2/1972 | Hodgson | |
| 4,112,213 A | 9/1978 | Waldman | |
| 4,310,509 A | 1/1982 | Berglund | |
| 4,323,557 A | 4/1982 | Rosso | |
| 4,364,995 A | 12/1982 | Crawford | |
| 4,472,480 A | 9/1984 | Olson | |
| 4,595,001 A | 6/1986 | Potter | |
| 4,664,859 A | 5/1987 | Knoop | |
| 4,737,410 A | 4/1988 | Kantner | |
| 5,088,483 A | 2/1992 | Heinecke | |
| 5,160,315 A | 11/1992 | Heinecke | |
| 5,429,591 A * | 7/1995 | Yamamoto ............ | A61F 13/023 424/448 |
| 5,622,711 A | 4/1997 | Chen | |
| 5,633,010 A | 5/1997 | Chen | |
| 5,681,575 A | 10/1997 | Burrell | |
| 5,753,251 A | 5/1998 | Burrell | |
| 5,888,594 A | 3/1999 | David | |
| 6,994,904 B2 | 2/2006 | Joseph | |
| 7,137,968 B1 * | 11/2006 | Burrell ................. | A61M 25/02 604/180 |
| 7,745,509 B2 | 6/2010 | Burton | |
| 8,460,568 B2 | 6/2013 | David | |
| 8,634,146 B2 | 6/2014 | David | |
| 2002/0192298 A1 | 12/2002 | Burrell | |

(Continued)

FOREIGN PATENT DOCUMENTS

| | | |
|---|---|---|
| WO | WO 2010-056541 | 5/2010 |
| WO | WO 2010-056543 | 5/2010 |
| WO | WO 2011-059915 | 5/2011 |

(Continued)

OTHER PUBLICATIONS

International Search Report for PCT International Application No. PCT/US2016/060317, dated Feb. 13, 2017, 5 pages.
International Search Report for PCT International Application No. PCT/US2016/061267, dated Feb. 13, 2017, 5 pages.

*Primary Examiner* — Susan T Tran
(74) *Attorney, Agent, or Firm* — Qiang Han

(57) ABSTRACT

An article having anti-microbial effect is provided. The article includes an occlusive layer; a substrate overlaying the occlusive layer, wherein the substrate having two opposing major surfaces; a metal oxide layer overlaying the substrate, wherein the metal oxide layer comprises a metal oxide and wherein the metal oxide layer comprises less than 40 wt. % non-oxidized metal; and a metal layer overlaying the metal oxide layer.

15 Claims, 1 Drawing Sheet

(56) References Cited

U.S. PATENT DOCUMENTS

2010/0304182 A1 12/2010 Facchini
2011/0262699 A1 10/2011 Yializis

FOREIGN PATENT DOCUMENTS

| WO | WO 2014-149718 | 9/2014 |
| WO | WO 2015-013387 | 1/2015 |
| WO | WO 2016-179396 | 11/2016 |
| WO | WO 2017-004231 | 1/2017 |
| WO | WO 2017-083482 | 5/2017 |

\* cited by examiner

ANTI-MICROBIAL ARTICLES AND METHODS OF USING SAME

BACKGROUND

The risk of being infected from medical devices is particularly high in the medical field. Anti-microbial articles or coatings are used extensively to prevent/reduce infections in the medical community. For example, medical devices used by doctors, including orthopedic pins, plates and implants, wound dressings, etc., must constantly guard against infection. Metallic ions with anti-microbial properties, such as Ag, Au, Pt, Pd, Ir, Cu, Sn, Sb, Bi and Zn, were used as anti-microbial compounds. Of these metallic ions, silver is known due to its good bioactivity. Various silver salts, complexes and colloids have been used to prevent and control infection.

SUMMARY

Although soluble salts of silver have been currently used to prevent microbial infections, they do not provide prolonged release of silver ions due to loss through removal or complexation of the free silver ions. They must be reapplied periodically to address this problem. Sometimes, reapplication is burdensome or sometimes even impractical, for example, when implanted medical devices are involved. Thus, it is desirable to have an anti-microbial article to provide a more effective release of anti-microbial agents.

In various exemplary embodiments described herein, the disclosed articles may be used to prevent microbial infections. The disclosed articles may be useful to provide an enhanced release of anti-microbial agents and thus to provide an increased anti-microbial activity.

In one aspect, the disclosure provides an article that includes an occlusive layer; a substrate overlaying the occlusive layer, wherein the substrate having two opposing major surfaces; a metal oxide layer overlaying the substrate, wherein the metal oxide layer comprises a metal oxide and wherein the metal oxide layer comprises less than 40 wt. % non-oxidized metal; and a metal layer overlaying the metal oxide layer.

Some other aspects of the present disclosure provide a method of using the article. The method can include providing the article of the present disclosure and applying the article to a subject; wherein the article exhibits a more than 4 log reduction of bacterial growth within 7 days.

Other features and aspects of the present disclosure will become apparent by consideration of the detailed description.

Definitions

Certain terms are used throughout the description and the claims that, while for the most part are well known, may require some explanation. It should be understood that, as used herein:

The terms "about" or "approximately" with reference to a numerical value or a shape means+/−five percent of the numerical value or property or characteristic, but also expressly includes any narrow range within the +/−five percent of the numerical value or property or characteristic as well as the exact numerical value. For example, a temperature of "about" 100° C. refers to a temperature from 95° C. to 105° C., but also expressly includes any narrower range of temperature or even a single temperature within that range, including, for example, a temperature of exactly 100° C.

The terms "a", "an", and "the" include plural referents unless the content clearly dictates otherwise. Thus, for example, reference to a material containing "a compound" includes a mixture of two or more compounds.

The term "or" is generally employed in its sense including "and/or" unless the content clearly dictates otherwise.

The term "wetting time" refers to the time period between when a drop of colored water is added to the surface of an article and when the water drop is completely absorbed into the article.

BRIEF DESCRIPTION OF THE DRAWINGS

The disclosure may be more completely understood in consideration of the following detailed description of various embodiments of the disclosure in connection with the accompanying drawings, in which it is to be understood by one of ordinary skill in the art that the drawings illustrate certain exemplary embodiments only, and are not intended as limiting the broader aspects of the present disclosure.

DETAILED DESCRIPTION

In the following description, reference is made to the accompanying set of drawings that form a part of the description hereof and in which are shown by way of illustration several specific embodiments. It is to be understood that other embodiments are contemplated and may be made without departing from the scope or spirit of the present invention. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. At the very least, and not as an attempt to limit the application of the doctrine of equivalents to the scope of the claimed embodiments, each numerical parameter should at least be construed in light of the number of reported significant digits and by applying ordinary rounding techniques. In addition, the use of numerical ranges with endpoints includes all numbers within that range (e.g. 1 to 5 includes 1, 1.5, 2, 2.75, 3, 3.80, 4, and 5) and any narrower range or single value within that range.

Various exemplary embodiments of the disclosure will now be described with particular reference to the Drawings. Exemplary embodiments of the present disclosure may take on various modifications and alterations without departing from the spirit and scope of the disclosure. Accordingly, it is to be understood that the embodiments of the present disclosure are not to be limited to the following described exemplary embodiments, but are to be controlled by the limitations set forth in the claims and any equivalents thereof.

Figure 1:
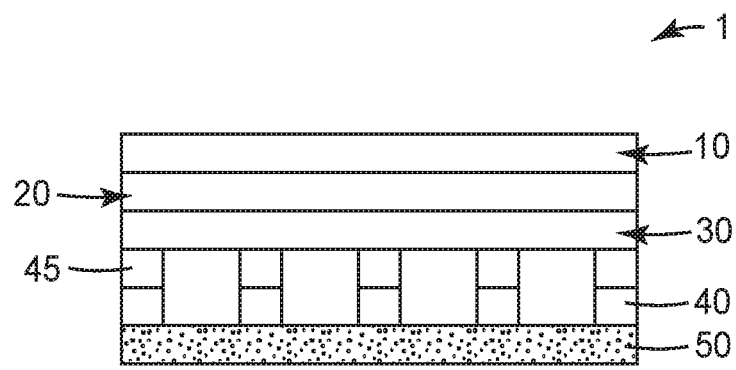
FIG. 1 is a cross-sectional view of an embodiment of an anti-microbial article of the present disclosure.

An article is disclosed herein. FIG. 1 is a cross-sectional view of an embodiment of article 1. Overall, article 1 includes an occlusive layer 10, a substrate 20 overlaying the occlusive layer, a metal oxide layer 30 overlaying the substrate and a metal layer 40 overlaying the metal oxide layer. The substrate has two opposing major surfaces. In the embodiment shown in FIG. 1, metal oxide layer 30 adjoins substrate 20 and metal layer 40 is next to metal oxide layer 30. The article may include an optional insulation coating layer 45 between metal oxide layer 30 and metal layer 40. Insulation coating layer can cover entire or part of metal layer. In some embodiments, the metal layer can be discontinuous or patterned, for examples as shown in in FIG. 1.

Figure 2:
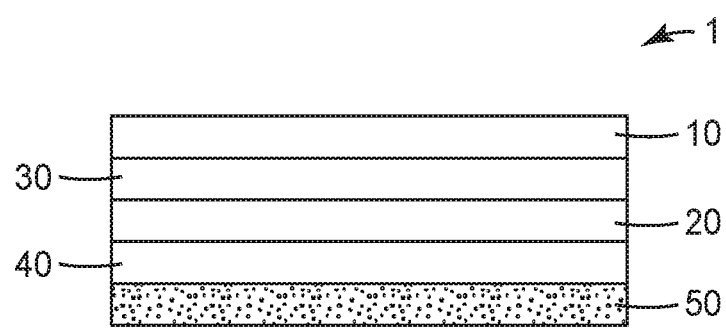
FIG. 2 is a cross-sectional view of an embodiment of an anti-microbial article of the present disclosure.

Alternatively, as shown in FIG. 2, the metal oxide layer 30 can be in direct contact one opposing major surface of the substrate 20 and the metal layer 40 can be in direct contact with the other opposing major surface of the substrate 20. In this embodiment, the metal layer can be discontinuous or continuous.

An additional adhesive layer 50 can be supplied to article 1 as shown in FIG. 1. In this embodiment, adhesive layer 50 covers the entire surface of metal layer 40. However, it is understood that the adhesive layer 50 may cover only a portion of the metal layer 40. The article may include an optional release liners (not shown) that covers all or a portion of the adhesives to prevent contamination of the adhesives. An optional carrier (not shown) may be included to cover all or a portion of occlusive layer 10, providing structural support if the article is thin and highly flexible. The carrier maybe removable from occlusive layer 10 once the article is placed on a subject.

The article of the present disclosure can be used to provide an anti-microbial effect. The article can be provided to a health care provider and can be applied to a subject to release anti-microbial agents.

Occlusive Layer

The occlusive layers are useful to provide an impermeable barrier to the passage of liquids and at least some gases. Representative barriers may include non-woven and woven fibrous webs, knits, films, foams polymeric films and other familiar backing materials. In some embodiments, a transparent occlusive layer is desirable to allow for viewing of the underlying subjects. Suitable occlusive layers may include those described in International Publication No. WO 2014/149718, the disclosures of which are hereby incorporated by reference.

In one embodiment, the occlusive layer has high moisture vapor permeability, but generally impermeable to liquid water so that microbes and other contaminants are sealed out from the area under the article. One example of a suitable material is a high moisture vapor permeable film such as described in U.S. Pat. Nos. 3,645,835 and 4,595,001, the disclosures of which are herein incorporated by reference. In one embodiment, the occlusive layer can be an elastomeric polyurethane, polyester, or polyether block amide films. These films combine the desirable properties of resiliency, elasticity, high moisture vapor permeability, and transparency. A description of this characteristic of occlusive layers can be found in issued U.S. Pat. Nos. 5,088,483 and 5,160,315, the disclosures of which are hereby incorporated by reference Commercially available examples of potentially suitable materials for the occlusive layer may include the thin polymeric film sold under the trade names TEGADERM (3M Company), OPSITE (Smith & Nephew), etc. Because fluids may be actively removed from the sealed environments defined by the article, a relatively high moisture vapor permeable occlusive layer may not be required. As a result, some other potentially useful materials for the occlusive layer may include, e.g., metallocene polyolefins and SBS and SIS block copolymer materials could be used.

Regardless, however, it may be desirable that the occlusive layer be kept relatively thin to, e.g., improve conformability. For example, the occlusive layer may be formed of polymeric films with a thickness of 200 micrometers or less, or 100 micrometers or less, 50 micrometers or less, or 25 micrometers or less.

Substrate

The substrate can be an absorbent substrate selected from foam, fabric, nonwoven, hydrocolloid, hydrogel, and combination of thereof. Exemplary absorbent substrate can include film, fabrics or porous article made from viscose, rayon, alginate, gauze, biopolymers, polyurethane, biodegradable polymers or the polymers described in U.S. Pat. No. 7,745,509, the disclosures of which is hereby incorporated by reference. The absorbent materials used in the absorbent substrate can be manufactured of any suitable materials including, but not limited to, woven or nonwoven cotton or rayon. Absorbent pad can be used as the absorbent layer and can be useful for containing a number of substances, optionally including drugs for transdermal drug delivery, chemical indicators to monitor hormones or other substances in a patient, etc.

The absorbent layer may include a hydrocolloid composition, including the hydrocolloid compositions described in U.S. Pat. Nos. 5,622,711 and 5,633,010, the disclosures of which are hereby incorporated by reference. The hydrocolloid absorbent may comprise, for example, a natural hydrocolloid, such as pectin, gelatin, or carboxymethylcellulose (CMC) (Aqualon Corp., Wilmington, Del.), a semi-synthetic hydrocolloid, such as cross-linked carboxymethylcellulose (X4ink CMC) (e.g. Ac-Di-Sol; FMC Corp., Philadelphia, Pa.), a synthetic hydrocolloid, such as cross-linked polyacrylic acid (PAA) (e.g., CARBOPOL™ No. 974P; B.F. Goodrich, Brecksville, Ohio), or a combination thereof. Absorbent layer can be manufactured of other synthetic and natural hydrophilic materials including polymer gels and foams.

Metal Oxide Layer

The metal oxide layer of the present disclosure includes a metal oxide. The metal oxide can be those known to have an anti-microbial effect. For most medical use, the metal oxide can also be biocompatible. In some embodiments, the metal oxide used in the metal oxide layer can include, but is not limited to, silver oxide, copper oxide, gold oxide, zinc oxide, magnesium oxide, titanium oxide, chromium oxide and combinations thereof. In some of these embodiments, the metal oxide can be silver oxide, including but not limited to, $Ag_2O$. In some embodiments, the metal oxide layer can include less than 40 wt. %, less than 20 wt. %, less than 10 wt. %, less than 5 wt. %, less than 1 wt. % non-oxidized metal. When the metal oxide layer includes more than 40 wt. % non-oxidized metal, the article will become more conductive, i.e., the resistivity of the article decreases, and the release of anti-microbial agents also decreases.

The metal oxide layer can be formed by any suitable means, for example, by physical vapor deposition techniques. The physical vapor deposition techniques can include, but is not limited to, vacuum or arc evaporation, sputtering, magnetron sputtering and ion plating. Suitable physical vapor deposition techniques can include those described in U.S. Pat. Nos. 4,364,995; 5,681,575 and 5,753,251, the disclosures of which are hereby incorporated by reference.

By the controlled introduction of reactive material, for example, oxygen into the metal vapor stream of vapor deposition apparatus during the vapor deposition of metals onto substrates, controlled conversion of the metal to metal oxides can be achieved. Therefore, by controlling the amount of the reactive vapor or gas introduced, the proportion of metal to metal oxide in the metal oxide layer can be controlled. For 100% conversion of the metal to metal oxides at a given level of the layer, at least a stoichiometric amount of the oxygen containing gas or vapor is introduced to a portion of the metal vapor stream. When the amount of the oxygen containing gas increases, the metal oxide layer will contain a higher weight percent of metal oxide. The ability to achieve release of metal atoms, ions, molecules or clusters on a sustainable basis can be effected by varying the amount of the oxygen containing gas. As the amount of metal oxide increases when the level of oxygen containing gas introduced increases, metal ions released from the article in turn increases. Thus, a higher weight percent of metal oxide can, for example, provide an enhanced release of anti-microbial agents, such as metal ions and provide an increased anti-microbial activity.

The metal oxide layer can be formed as a thin film. The film can have a thickness no greater than that needed to provide release of metal ions on a sustainable basis over a suitable period of time. In that respect, the thickness will vary with the particular metal in the coating (which varies the solubility and abrasion resistance), and with the amount of the oxygen containing gas or vapor introduced to the metal vapor stream. The thickness will be thin enough that the metal oxide layer does not interfere with the dimensional tolerances or flexibility of the article for its intended utility. Typically, the metal oxide layer has a thicknesses of less than 1 micron. However, it is understood that increased thicknesses may be used depending on the degree of metal ion release needed over a period of time.

Metal Layer

The metal layer of the present disclosure includes a metal. The metal can be those known to have a positive electric potential. In some embodiments, the metal oxide used in the metal oxide layer can include, but is not limited to, zinc, magnesium, aluminum, iron, calcium, tin, copper, titanium, chromium, nickel and alloys thereof. The metal oxide layer can be formed by any suitable means, for example, by vapor deposition techniques. The vapor deposition techniques can include, but is not limited to, vacuum or arc evaporation, sputtering, magnetron sputtering and ion plating. Suitable physical vapor deposition techniques can include those described in U.S. Pat. Nos. 4,364,995; 5,681,575 and 5,753,251, the disclosures of which are hereby incorporated by reference.

Optional Components

Suitable polymer for use in the insulation coating layer can include polyethylene terephthlate, polystyrene, acrlonitrile butabiene styrene, polyvinyl chloride, polyvinylidene chloride, polycarbonate, polyacrylates, polyurethanes, polyvinyl acetate, polyvinyl alcohol, polyamide, polyimide, polypropylene, polyester, polyethylene, poly(methyl methacrylate), polyethylene naphthalate, styrene acrylonitrile copolymer, silicone-polyoxiamide polymers, fluoropolymers, cellulose triacetate polymer, cyclic olefin copolymers and thermoplastic elastomers. The insulation coating layer can be formed by any suitable means, including extrusion, solvent casting, or lamination process described in U.S. Pat. Nos. 3,415,920, 4,664,859 and 3,416,525.

Suitable adhesive for use in the article includes any adhesive that provides acceptable adhesion to skin and is acceptable for use on skin (e.g., the adhesive should preferably be non-irritating and non-sensitizing). Suitable adhesives are pressure sensitive and in certain embodiments have a relatively high moisture vapor transmission rate to allow for moisture evaporation. Suitable pressure sensitive adhesives include those based on acrylates, urethane, hyrdogels, hydrocolloids, block copolymers, silicones, rubber based adhesives (including natural rubber, polyisoprene, polyisobutylene, butyl rubber etc.) as well as combinations of these adhesives. The adhesive component may contain tackifiers, plasticizers, rheology modifiers as well as active components including for example an antimicrobial agent. Suitable adhesive can include those described in U.S. Pat. Nos. 3,389,827; 4,112,213; 4,310,509; 4,323,557; 4,595,001; 4,737,410; 6,994,904 and International Publication Nos. WO 2010/056541; WO 2010/056543 and WO 2014/149718, the disclosures of which are hereby incorporated by reference.

Suitable release liners can be made of kraft papers, polyethylene, polypropylene, polyester or composites of any of these materials. In one embodiment, the package that contains the adhesive dressing may serve as a release liner. In one embodiment, the liners are coated with release agents such as fluorochemicals or silicones. For example, U.S. Pat. No. 4,472,480, the disclosure of which is hereby incorporated by reference, describes low surface energy perfluorochemical liners. In one embodiment, the liners are papers, polyolefin films, or polyester films coated with silicone release materials.

The carrier used in the article can be constructed of any suitable materials such as fabric that are woven or kitted, nonwoven material, papers, or film. In one embodiment, the carrier is along the perimeter of the occlusive layer and is removable from the occlusive layer, similar to the carrier used the 3M Tegaderm™ Transparent Film Dressing, available from 3M Company, St. Paul, Minn.

Properties

The anti-microbial effect of the article can be achieved, for example, when the article is brought into contact with an alcohol or a water based electrolyte such as, a body fluid or body tissue, thus releasing metal ions such as $Ag^+$, atoms, molecules or clusters. The concentration of the metal which is needed to produce an anti-microbial effect will vary from metal to metal. Generally, anti-microbial effect is achieved in body fluids such as plasma, serum or urine at concentrations less than 10 ppm. In some embodiments, $Ag^+$ release concentration from the article can be 0.1 ppm, 0.5 ppm, 1 ppm, 2 ppm, 2.5 ppm, 3 ppm, 4 ppm, 5 ppm, 6 ppm, 7 ppm, 8 ppm, 9 ppm, 10 ppm, 20 ppm, 40 ppm or a range between and including any two of these values. As discussed above, when the amount of metal oxide in the metal oxide layer increases, the metal ions released from the article in turn increases. For example, a more than 60 wt. % metal oxide provides an enhanced release of metal ions from the article. Therefore, the article of the present disclosure can provide a very effective anti-microbial effect. In some embodiments, the article can exhibit a more than 4 log reduction of bacterial growth within 7 days.

The can generate at least one electrical current when introduced to an electrolytic solution. In the presence of an electrically conducting solution, redox reactions may take place, and thus currents may be produced between the metal oxide layer and the metal layer. For example, when the metal oxide layer includes silver oxide and the metal layer includes zinc, silver oxide is the cathode (positive electrode) and zinc is the anode (negative electrode), because the electrons follow from zinc to silver oxide. The flow of ions generates the electrical current. Thus, when the article of the present application is used as a wound dressing, it can recreate a physiologic current, which is important to the induction of neutrophil, macrophage and fibroblast cells essential to the healing process. In addition, the current can stimulates regional nerve endings to promote their involvement in wound resolution.

In some embodiments, the article of the present disclosure can have a more than 50%, more than 100%, more than 150%, more than 200%, more than 300%, more than 400%, more than 500%, or more than 600% absorbency. Absorbency of the article generally relates to the capacity of absorbing wound fluid (exudate), when the article is used as a medical dressing. Articles with a high absorbency can absorb more exudate. This can, for example, help decrease the risk of maceration and irritation to the wound and surrounding tissues and the frequency of replacing the articles. In some embodiments, the article of the present disclosure can have a less than 3 minutes, less than 2 minutes, or less than 1 minute wetting time. Wetting time of the article generally relates to the absorption rate of fluid into the article. Shorter wetting time can enhance the overall fluid management profile, for example, increasing the timer interval between replacing the articles. At the early stage of healing a wound, the article with a shorter wetting time can quickly remove fluid, which in turns minimizes the potential risk of infection.

Various exemplary embodiments of the present disclosure are further illustrated by the following listing of embodiments, which should not be construed to unduly limit the present disclosure:

EMBODIMENTS

1. An article comprising:
   an occlusive layer;
   a substrate overlaying the occlusive layer, wherein the substrate having two opposing major surfaces;
   a metal oxide layer overlaying the substrate, wherein the metal oxide layer comprises a metal oxide and wherein the metal oxide layer comprises less than 40 wt. % non-oxidized metal; and
   a metal layer overlaying the metal oxide layer.
2. The article of embodiment 1, wherein the metal layer adjourns the metal oxide layer.
3. The article of any of embodiments 1 to 2, wherein the metal layer is discontinuous or patterned.
4. The article of embodiment 1, wherein the metal oxide layer is in direct contact with one opposing major surface of the substrate and the metal layer is in direct contact with the other opposing major surface of the substrate.
5. The article of any embodiments 1 to 4, wherein the substrate is an absorbent substrate selected from foam, fabric, nonwoven, hydrocolloid, hydrogel, and combination of thereof.
6. The article of any of embodiments 1 to 5, wherein the metal oxide is selected from silver oxide, copper oxide, gold oxide, platinum oxide, zinc oxide, magnesium oxide, titanium oxide, chromium oxide and combinations thereof.
7. The article of embodiment 6, wherein the metal oxide is silver oxide.
8. The article of embodiment 7, wherein the silver oxide is $Ag_2O$.
9. The article of any of embodiments 1 to 8, wherein the metal layer comprises a metal and the metal is selected from zinc, magnesium, aluminum, iron, calcium, tin, copper, titanium, chromium, nickel and alloys thereof.
10. The article of any of embodiments 1 to 9, wherein the metal oxide layer is formed by vapor deposition.
11. The article of any of embodiments 1 to 10, wherein the article exhibits a more than 4 log reduction of bacterial growth within 7 days.
12. The article of any of embodiments 1 to 11, wherein $Ag^+$ release concentration of the article is more than 0.1 ppm.
13. The article of embodiment 12, wherein $Ag^+$ release concentration of the article is more than 2.5 ppm.
14. The article of embodiment 13, wherein $Ag^+$ release concentration of the article is more than 3 ppm.
15. The article of any of embodiments 1 to 14, wherein wetting time of the article is less than 3 minutes.
16. The article of any of embodiments 1 to 15, wherein wetting time of the article is less than 2 minutes.
17. The article of any of embodiments 1 to 16, wherein the article is capable of generating at least one electrical current when introduced to an electrolytic solution.
18. A method of use the article of embodiment 1, comprising of
   providing the article of embodiment 1; and
   applying the article to a subject;
   wherein the article exhibits a more than 4 log reduction of bacterial growth within 7 days.

EXAMPLES

These Examples are merely for illustrative purposes and are not meant to be overly limiting on the scope of the appended claims. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. At the very least, and not as an attempt to limit the application of the doctrine of equivalents to the scope of the claims, each numerical parameter should at least be construed in light of the number of reported significant digits and by applying ordinary rounding techniques.

Unless otherwise noted, all parts, percentages, ratios, etc. in the Examples and the rest of the specification are provided on the basis of weight. Solvents and other reagents used may be obtained from Sigma-Aldrich Chemical Company (Milwaukee, Wis.) unless otherwise noted.

Materials

| Material | Supplier |
| --- | --- |
| Eyesaline ® | Honeywell, Platteville, WI |
| 3M Super 77 Multipurpose Adhesive | 3M, St. Paul, MN |
| Polypropylene (PP) netting | Delstar, Wilmington, DE under the trade designation TK16-459 |
| Urethane Aero Foam | 3M, St. Paul, MN |

Sputtering Deposition Process

Silver films were coated onto 152 mm by 152 mm substrates by magnetron physical vapor deposition. The films were sputtered from a 76.2 mm round silver target in a batch coater. The substrate was placed on a substrate holder set up inside a vacuum chamber with a sputtering metal target located at a height of 228.6 mm above the substrate holder. After the chamber was evacuated to $2\times10^{-5}$ torr base pressure, sputter gases of argon (71% by flow rate) and reactive oxygen (29% by flow rate) were admitted inside the chamber and total pressure of the chamber was adjusted to 5 millitorr. Sputtering was initiated using a DC power supply at a constant power level of 0.25 kilowatts. The sputtering duration was varied to produce a same coating weight per unit area of 0.05 mg/cm$^2$.

Copper films were sputtered from a 76.2 mm round copper target in a batch coater. The substrate was placed on a substrate holder set up inside a vacuum chamber with a sputtering metal target located at a height of 228.6 mm above the substrate holder. After the chamber was evacuated to 2×10-5 torr base pressure, argon was admitted inside the chamber and total pressure of the chamber was adjusted to 1.6 millitorr. Sputtering was initiated using a DC power supply at a constant power level of 0.50 kilowatts for 5 minutes and 30 seconds.

Zinc films were sputtered from a 76.2 mm round zinc target in a batch coater. The substrate was placed on a substrate holder set up inside a vacuum chamber with a sputtering metal target located at a height of 228.6 mm above the substrate holder. After the chamber was evacuated to 2×10-5 torr base pressure, argon was admitted inside the chamber and total pressure of the chamber was adjusted to 1.6 millitorr. Sputtering was initiated using a DC power supply at a constant power level of 0.50 kilowatts for 1 minutes and 30 seconds.

Magnesium films were sputtered from a 76.2 mm round magnesium target in a batch coater. The substrate was placed on a substrate holder set up inside a vacuum chamber with a sputtering metal target located at a height of 228.6 mm above the substrate holder. After the chamber was evacuated to 2×10-5 torr base pressure, argon was admitted inside the chamber and total pressure of the chamber was adjusted to 1.6 millitorr. Sputtering was initiated using a DC power supply at a constant power level of 0.50 kilowatts for 15 minutes.

Lamination Process

Metallized polypropylene nettings were laminated to silver coat foam substrates using 3M Super 77 Multipurpose Adhesive (3M, St. Paul, Minn.).

Measurement of Micro-Current

Samples were pre-wetted with Eyesaline® (Honeywell, Platteville, Wis.). Micro-current was then measured using WAVETEK DM25XT multi-meter with two-point probes (Wavetek, San Diego, Calif.).

Log Reduction Testing Method

The JIS Z 2801 test method (modified) (Japan Industrial Standards; Japanese Standards Association; Tokyo, JP) was used to evaluate the antibacterial activity of antibacterial of coatings. The bacterial inoculum was prepared in a solution of 1 part Nutrient Broth (NB) and 499 parts phosphate buffer. A portion of the bacterial suspension (150 ul) was placed onto the surface of the article and the inoculated article was incubated for the specified contact time at 27+/−1° C. After incubation, the article was placed into 20 ml of D/E Neutralizing Broth. The number of surviving bacteria in the Neutralizing broth was determined by using 3M Petrifilm.

Measurement of Ag$^+$ Release

The electrode (Orion Sure-flow IonPlus Silver/Sulfide combination ion selective electrode, model 9616BN) slope was checked. Ag$^+$ standard solutions were prepared. The electrode was calibrated daily by immersion in 0.3, 1, 10, and 100 ppm Ag$^+$ standard solutions. The silver ion release of the article was evaluated as follows. 60 mL of water, 1 mL ISA, and 50 μL of the 1000 ppm silver standard solution were added to a 100 mL disposable beaker and a stir bar was added. The initial potential on the Ag ISE was recorded. 3 cm$^2$ of the article was added to the beaker and the timer started. Free silver ion concentration in solution was recorded at ten second intervals by the Tiamo 2.4 software (from Metrohm, Herisau, Switzerland) for 60 minutes.

Substrate Wetting Time (Time to Complete Immersion) Test

Wetting time was measured by adding a drop of colored water to silver coated absorbent article and recording the time when the water drop was completely absorbed into the article.

Examples 1-3 & Comparative 1

Ag was deposited on Urethane Aero Foam using the sputtering process described above at the pressure of 5 millitorr. PP nettings were coated with copper, magnesium or zinc according to the methods described above. The nettings with and without metal coating were laminated to Ag coat Aearo Foam using 3M Super 77 multipurpose adhesive. Microcurrent and log reduction properties are measured and reported in Table 1

TABLE 1

Microcurrent and log reduction results for Comparative 1 and Samples 1-3

| | Construction | Microcurrent (milli Volt) | S. aureus ATCC6538 Log Reduction CFU/cm2 (24 hours) |
|---|---|---|---|
| Comparative 1 | (PP netting-adhesive)/(Ag coating-Aearo Foam) | 0 | 2.48 |
| Example 1 | (Copper coating-PP netting-adhesive)/(Ag coating-Aearo Foam) | 8 | 2.86 |
| Example 2 | (Zinc coating-PP netting-adhesive)/(Ag coating-Aearo Foam) | 50 | 3.85 |
| Example 3 | (Magnesium coating-PP netting-adhesive)/(Ag coating-Aearo Foam) | 1000 | 4.67 |

All references and publications cited herein are expressly incorporated herein by reference in their entirety into this disclosure. Illustrative embodiments of this invention are discussed and reference has been made to possible variations within the scope of this invention. For example, features depicted in connection with one illustrative embodiment may be used in connection with other embodiments of the invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. An article comprising:
an occlusive layer;
a substrate overlaying the occlusive layer, wherein the substrate having two opposing major surfaces;
a metal oxide layer overlaying the substrate, wherein the metal oxide layer comprises a metal oxide and wherein the metal oxide layer comprises less than 40 wt. % non-oxidized metal; and
a metal layer overlaying the metal oxide layer.

2. The article of claim 1, wherein the metal layer adjourns the metal oxide layer.

3. The article of claim 1, wherein the metal layer is discontinuous or patterned.

4. The article of claim 1, wherein the metal oxide layer is in direct contact with one opposing major surface of the substrate and the metal layer is in direct contact with the other opposing major surface of the substrate.

5. The article of claim 1, wherein the substrate is an absorbent substrate selected from foam, fabric, nonwoven, hydrocolloid, hydrogel, and combination of thereof.

6. The article of claim 1, wherein the metal oxide is selected from silver oxide, copper oxide, gold oxide, platinum oxide, zinc oxide, magnesium oxide, titanium oxide, chromium oxide and combinations thereof.

7. The article of claim 6, wherein the metal oxide is silver oxide.

8. The article of claim 7, wherein the silver oxide is $Ag_2O$.

9. The article of claim 1, wherein the metal layer comprises a metal and the metal is selected from zinc, magnesium, aluminum, iron, calcium, tin, copper, titanium, chromium, nickel and alloys thereof.

10. The article of claim 1, wherein the metal oxide layer is formed by vapor deposition.

11. The article of claim 1, wherein the article exhibits a more than 4 log reduction of bacterial growth within 7 days.

12. The article of claim 1, wherein $Ag^+$ release concentration of the article is more than 0.1 ppm.

13. The article of claim 1, wherein wetting time of the article is less than 3 minutes.

14. The article of claim 1, wherein the article is capable of generating at least one electrical current when introduced to an electrolytic solution.

15. A method of use the article of claim 1, comprising of
providing the article of claim 1; and
applying the article to a subject;
wherein the article exhibits a more than 4 log reduction of bacterial growth within 7 days.

* * * * *